(12) United States Patent
Chuang et al.

(10) Patent No.: US 7,609,373 B2
(45) Date of Patent: Oct. 27, 2009

(54) REDUCING VARIATIONS IN ENERGY REFLECTED FROM A SAMPLE DUE TO THIN FILM INTERFERENCE

(75) Inventors: Yung-Ho Chuang, Cupertino, CA (US); J. Joseph Armstrong, Milpitas, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 11/223,851

(22) Filed: Sep. 9, 2005

(65) Prior Publication Data

US 2006/0268265 A1   Nov. 30, 2006

Related U.S. Application Data

(60) Provisional application No. 60/686,237, filed on May 31, 2005.

(51) Int. Cl.
 *G01N 21/00* (2006.01)
(52) U.S. Cl. .................................... 356/237.2; 356/445
(58) Field of Classification Search ... 356/237.1–237.5, 356/445–448
 See application file for complete search history.

(56) References Cited

U.S. PATENT DOCUMENTS

| | | | |
|---|---|---|---|
| 4,893,932 A | 1/1990 | Knollenberg | |
| 5,209,813 A | 5/1993 | Oshida et al. | |
| 5,302,839 A | 4/1994 | Kaise et al. | |
| 5,333,052 A | 7/1994 | Finarov | |
| 5,516,608 A | 5/1996 | Hobbs et al. | |
| 5,552,327 A | 9/1996 | Bachmann et al. | |
| 5,712,701 A | 1/1998 | Clementi et al. | |
| 5,757,494 A | 5/1998 | Green et al. | |
| 5,798,829 A | 8/1998 | Vaez-Iravani | |
| 5,838,433 A | 11/1998 | Hagiwara | |
| 5,903,342 A | 5/1999 | Yatsugake et al. | |
| 6,034,776 A | 3/2000 | Germer et al. | |
| 6,191,849 B1 | 2/2001 | Maeshima et al. | |
| 6,256,092 B1 | 7/2001 | Tomita et al. | |
| 6,384,909 B2 | 5/2002 | Tomita et al. | |
| 6,501,545 B2 | 12/2002 | Komuro et al. | |
| 6,538,730 B2 | 3/2003 | Vaez-Iravani et al. | |
| 6,678,043 B1 | 1/2004 | Vurens et al. | |
| 6,683,683 B2 | 1/2004 | Tomita et al. | |
| 6,762,831 B2 | 7/2004 | Shibata et al. | |
| 6,774,987 B2 | 8/2004 | Komatsu et al. | |
| 7,161,671 B2 * | 1/2007 | Shibata et al. | ........... 356/237.2 |
| 2004/0145734 A1 | 7/2004 | Shibata et al. | |
| 2004/0257560 A1 | 12/2004 | Shibata et al. | |
| 2005/0007580 A1 | 1/2005 | MacGibbon et al. | |
| 2005/0110988 A1 * | 5/2005 | Nishiyama et al. | ....... 356/237.5 |
| 2005/0237537 A1 * | 10/2005 | Leizerson et al. | ........... 356/504 |

* cited by examiner

*Primary Examiner*—Michael P Stafira
(74) *Attorney, Agent, or Firm*—Smyrski Law Group, A P.C.

(57) ABSTRACT

A system and method for inspecting a multi-layer sample, such as a silicon wafer, is disclosed. The design reduces variations in total reflected energy due to thin film interference. The design includes illuminating the sample at two incident angle ranges, where the two incident angle ranges are such that variation in total reflected energy at a first incident angle range may be employed to balance variation in total reflected energy at a second incident angle range. Defects are detected using die-to-die subtraction of the sample illuminated at the two incident angle ranges.

23 Claims, 14 Drawing Sheets

REDUCING VARIATIONS IN ENERGY REFLECTED FROM A SAMPLE DUE TO THIN FILM INTERFERENCE

This application claims the benefit of U.S. Provisional Patent Application 60/686,237, "Reducing Variations in Thin Film Energy Reflected from a Sample Due to Thin Film Interference," inventors J. Joseph Armstrong et al., filed May 31, 2005.

BACKGROUND OF THE INVENTION

1. Field of the Invention

The present invention relates generally to the field of optical imaging, and more specifically to optical systems used for microscopic imaging, inspection, metrology and lithography applications.

2. Description of the Related Art

Semiconductor wafers are composed of multiple thin film layers. These thin film layers are deposited or created and subsequently patterned one at a time. Creating and patterning each thin film layer of the wafer requires inspecting and identifying defects in the patterns for each thin film layer. The manufacturing and patterning process also entails adding a layer of photosensitive material or photoresist over the top of a thin film layer. The photoresist is then exposed to patterned light, and the photoreresist exposed to the patterned light may be removed and used as a mask. Any remaining photoresist operates as a mask to prevent etching of the underlying thin film. The underlying film may be etched and the remaining photoresist removed. The result is a pattern in the underlying thin film. Modern semiconductor reticles require advanced film products and processes, such as phase shift layers, to enhance their performance. These advanced products and processes can suffer from thin film effects.

Current wafer inspection systems primarily detect defects on individual layers using comparison techniques, such as a comparison between dies. This is commonly referred to as die-to-die subtraction. In die-to-die subtraction, the images of dies 1 and 2 are subtracted a difference may be identified between the images at location A. If the images of dies 2 and 3 are then subtracted and a difference is also found at location A, the defect is attributed to die 2 at location A.

Thin film interference effects limit the effectiveness of defect detection using the die-to-die subtraction technique, particularly in the presence of narrow band light. The thickness of the uppermost thin film layer can vary, and variations in thickness can change the reflected light level, providing a tendency to skew measurements. If a thickness variation exists from one die to the next, the thickness variation can produce additional variations in the die-to-die subtraction. Compensating for this effect requires adding the resultant difference to the defect detection threshold, thereby limiting the sensitivity of the defect detection procedure.

Interference effects can therefore adversely affect overall performance of a die to die comparison and ultimately the ability to inspect the wafer for defects. Certain illumination modes can enhance the overall inspection, and use of different illumination modes and techniques can in some cases significantly affect interference effects.

It would be beneficial to provide a system and method for use in microscopy that reduces or eliminates the effects of interference and overcomes the foregoing drawbacks present in previously known systems. Such a system may provide improved functionality over devices exhibiting those negative aspects described herein.

SUMMARY OF THE INVENTION

According to a first aspect of the present design, there is provided a method to reduce variations in total reflected energy due to thin film interference when inspecting a sample. The method comprises producing p-polarized light based on at least one from a group comprising linear, circular, and random polarized light, and illuminating the sample at an incident angle similar to Brewster's angle for a top most film. The illuminating uses p-polarized light from the producing wherein the p-polarized light is p-polarized relative to the sample.

According to a second aspect of the present design, there is provided a method to reduce variations in total reflected energy due to thin film interference for inspection of a sample. The method comprises illuminating the sample at two incident angle ranges, where the two incident angle ranges are such that variation in total reflected energy at a first incident angle range may be employed to balance variation in total reflected energy at a second incident angle range. Defects are detected using die-to-die subtraction of two samples both illuminated at the two incident angle ranges.

These and other aspects of the present invention will become apparent to those skilled in the art from the following detailed description of the invention and the accompanying drawings.

DESCRIPTION OF THE DRAWINGS

The present invention is illustrated by way of example, and not by way of limitation, in the figures of the accompanying drawings in which.

DETAILED DESCRIPTION OF THE INVENTION

The present design is a method and apparatus to reduce variations in energy reflected from a thin film used in fabricating a semiconductor wafer, where the variations result from changes in the film thickness of a sample. This effect is commonly called "thin film interference" and is particularly of interest when inspecting using a narrow band illumination source such as a laser. In the field of semiconductor wafer inspection, use of a narrow band illumination source can improve the signal-to-noise ratio of defects when using die-to-die subtraction techniques. The present design reduces or eliminates the effects of thin film interference when using die-to-die subtraction in the inspection of thin film layers.

The energy reflected from a sample for a given film thickness is a function of the angle, polarization, and wavelength of the transmitted illumination, as well as the properties of the thin film material employed. Since the thin film material is a given quantity that cannot be changed, only the range of illumination angles, illumination polarization, and illumination wavelength can be altered to address the effects of thin film interference. Specific combinations of these illumination parameters can, in certain cases, reduce or eliminate the effects of thin film interference.

Figure 1:
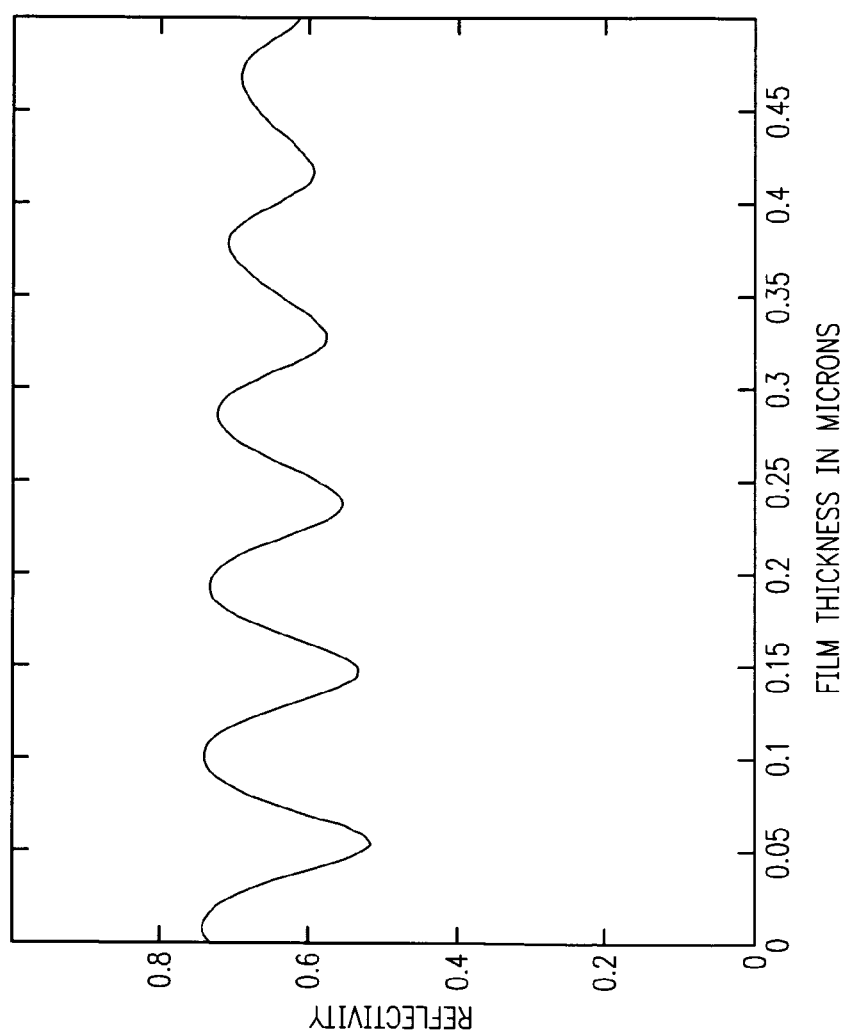
FIG. 1 is a graph of typical variations in the total reflected energy for linear polarization with silicon.

An example of typical variations in the energy reflected from a sample due to thin film interference is shown in FIG. 1. The sample represented in FIG. 1 is a silicon wafer with a top layer of silicon dioxide film. In the embodiment shown in FIG. 1, the film thickness varies from 0 to 0.5 microns. The illumination employed is narrow band, at a wavelength of 266 nm using linear polarization. The illumination includes all incident angles up to 0.9 NA (numerical aperture), or incident angles from 0 degrees up to 64 degrees, and all azimuthal angles. The reflectivity oscillates as the film thickness changes and ranges from a maximum of 0.74 to a minimum of 0.52 and has a period of about 0.1 microns.

The embodiment shown in FIG. 1 can provide reflected energy benefits when using die-to-die subtraction to detect defects. For an average film thickness of silicon dioxide of 170 nm, with film thickness variations from one die to the next by +/−2 nm, the reflected energy can vary by up to three percent. A three percent variance can be a dominant noise source, for example, in the presence of typical defect detection thresholds of less than 10 percent.

The present design reduces the effects of thin film interference by selecting illumination modes that tend to minimize variations in the energy reflected from the sample as the film thickness varies. The present design employs specific combinations of incidence angles and polarization depending on the illumination wavelength and the thin film materials.

The present design structures the illumination so that variations in the energy reflected from one portion of the illumination will compensate for variations in the energy reflected in another portion of the illumination. For example, if the reflectivity for a specific angle and polarization increases with increasing film thickness and the reflectivity for another angle and polarization decreases with increasing film thickness, these two illumination portions can be combined to compensate for each other over a range of film thickness values.

Figure 2:
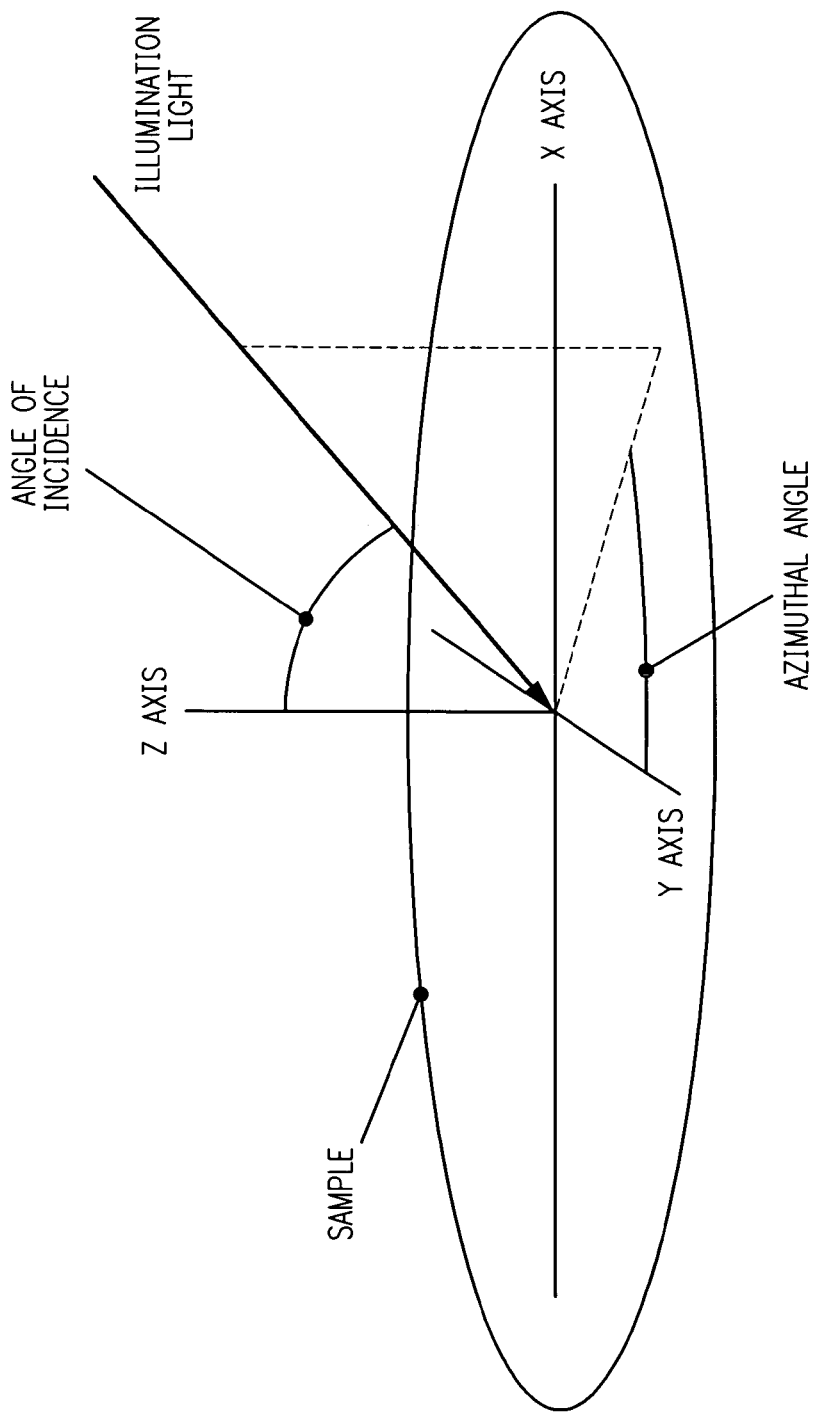
FIG. 2 illustrates definitions for the coordinate system above the sample.

The illumination angles above the sample are defined as shown in FIG. 2. The angle of incidence is the angle between the Z axis and the illumination light. In this embodiment, the Z axis is perpendicular to the sample and the X and Y axes lie in the plane of the sample. The azimuthal angle describes the angle of illumination with respect to the Y axis. Angle of illumination can range from zero degrees, where the illumination is along the positive Y axis, up to 359 degrees. Rotation is about the Z axis.

Ring illumination can them be described as a single angle of incidence above the sample covering all azimuthal angles. Ring illumination can also comprise a range of incident angles that cover all azimuthal angles.

The first embodiment of an illumination mode uses pure p-polarization, also called radial polarization because the electric field oscillates radially about the Z axis in a manner similar to spokes in a wheel. P-polarized light in the present design may be obtained efficiently by a variety of different techniques, including but not limited to producing p-polarized light based on linear, circular, or random polarized light.

Figure 3:
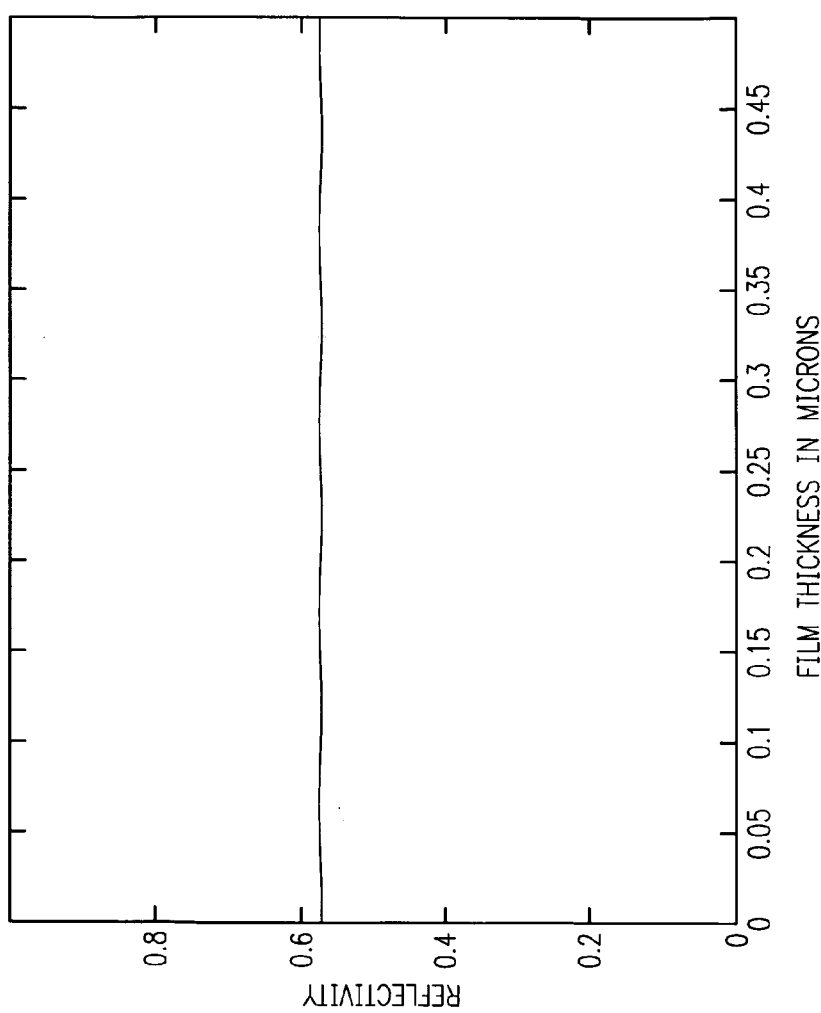
FIG. 3 is a graph of reflectivities for p-polarization at Brewster's angle for silicon dioxide on silicon at a wavelength of 266 nm.

Using radial polarization at an angle of incidence equal to Brewster's angle for the film on the sample provides no interference for any value of the film thickness. Brewster's angle, as known to those skilled in the art, represents the angle of incidence at which transmittance from one medium to another medium is one when the wavefront is linearly polarized with an electric field vector parallel to the plane of incidence. The lack of interference results from no receipt of a reflected component of the electric field from the first surface. FIG. 3 shows an example of this illumination using p-polarization, Brewster's angle illumination, a 266 nm wavelength, and a silicon dioxide film on a silicon substrate. This illumination can be from one azimuthal angle, multiple azimuthal angles, or from all azimuthal angles in a ring configuration.

Figure 4:
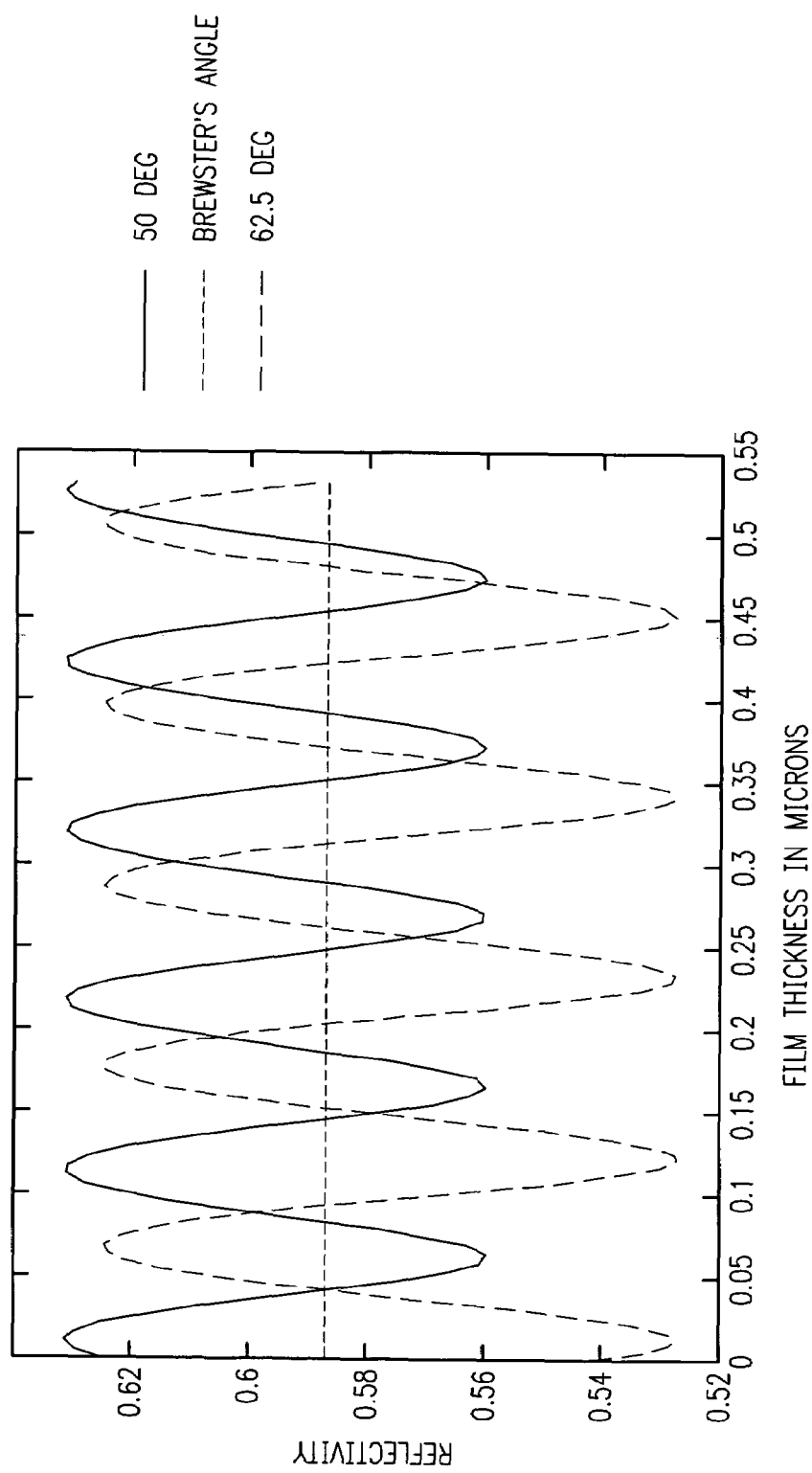
FIG. 4 is a graph of reflectivities for p-polarization at 50 degrees angle of incidence, Brewster's angle, and 62.5 degrees for silicon dioxide film on silicon at 266 nm wavelength.

The second embodiment of the current design is an illumination mode that uses two ranges of incident angles for illumination. In this mode, variations in energy reflected from one range of incident angles compensate for variations in the energy reflected from another range of incident angles. The mode shown uses p-polarized light for both ranges of incident angles. In this example, one range may include incident angles less than Brewster's angle and the other may include incident angles that are greater than Brewster's angle. As the film thickness varies, the energy reflected by the different angle ranges change with opposite signs, and the illumination energy portions can compensate for each other. Compensation in this manner is shown in FIG. 4. Reflectivity for Brewster's angle does not change as a function of the film thickness. In the embodiment shown, Brewster's angle is 56.3 degrees. The changes in reflectivity for the angles of 50 degrees and 62.5 degrees are also shown. Both of these reflectivities change in a sinusoidal fashion as the thickness of film increases. Near zero film thickness, the sinusoidal variation for the 50 degree angle of incidence is close to 180 degrees out of phase with the 62.5 degree angle of incidence, allowing for good interference cancellation.

The period of the sinusoidal variation differs between the 50 degree angle of incidence and the 62.5 degree angle of incidence. The difference in period length results from an increase in the optical path for the larger angle increases as the film thickness increases. Difference in period length can reduce the effectiveness of the cancellation for very thick films.

Figure 5:
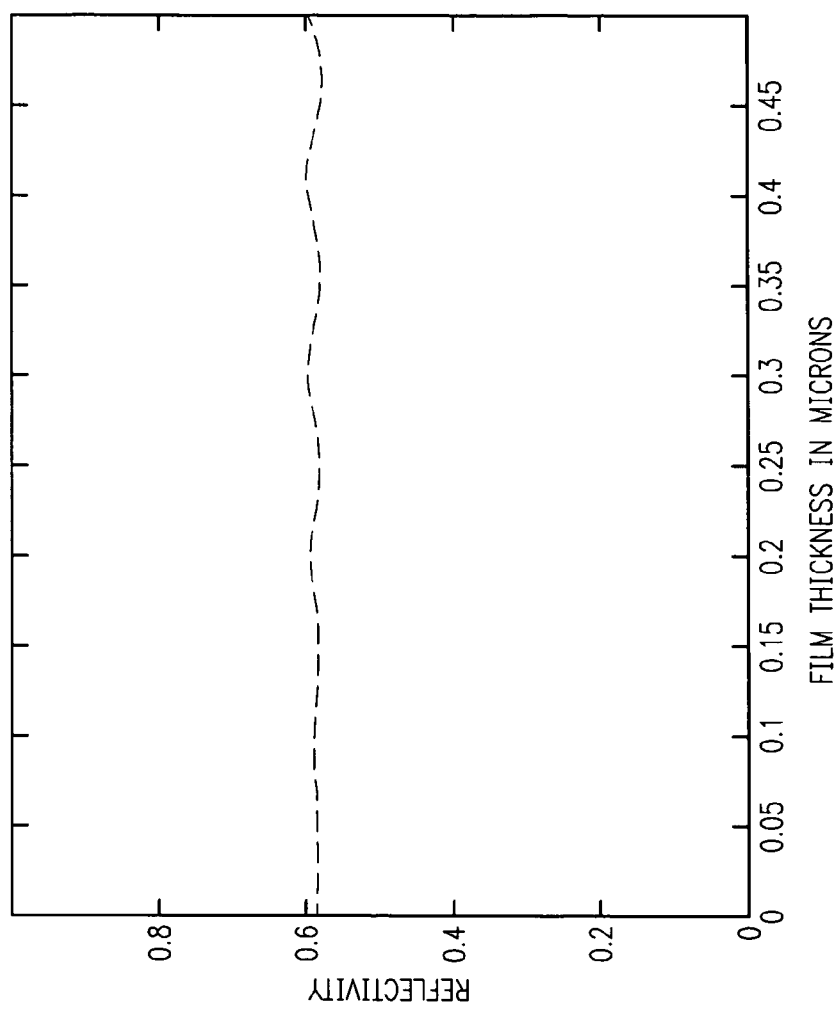
FIG. 5 is a graph of reflectivities for p-polarization using a ring from 50 degrees up to 62.5 degrees, including Brewster's angle at 56.3 degrees for silicon dioxide film on silicon substrate.

The result of using two ranges of incident angles is shown in FIG. 5. Incident angle ranges are from 50 degrees up to Brewster's angle at 56.3 degrees and from Brewster's angle up to 62.5 degrees, or a continuous angle of incidence from 50 degrees to 62.5 degrees. In this example the illumination uses all azimuthal angles to produce a uniform ring of p-polarized light. The variation in the energy reflected from the film is very constant up to 0.25 microns. For thicker films, other incident angle ranges can be used to produce less variation. Other incident angle ranges and polarizations can be employed to reduce variations in energy reflected from a thin film.

Figure 6:
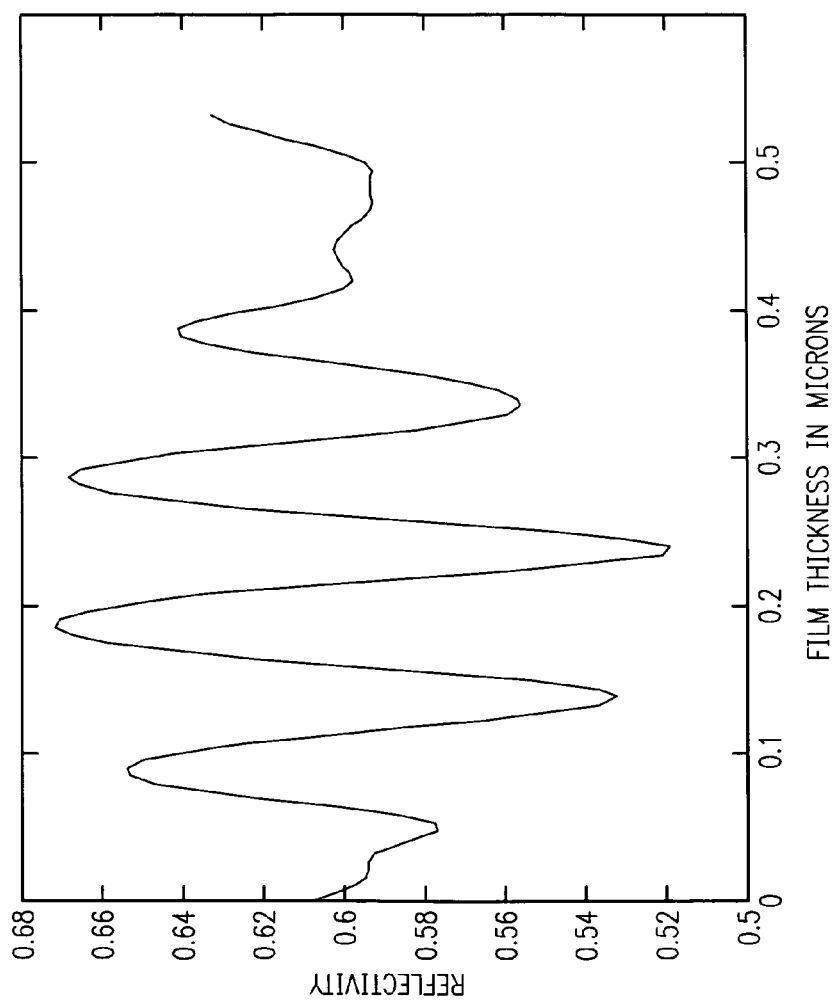
FIG. 6 is a graph of reflectivities for p-polarization using two rings for silicon dioxide film on silicon substrate.

The third embodiment employs illumination using two ranges of incident angles. In this mode, variations in the energy reflected from one range of incident angles compensates for the variations in the energy reflected from another range of incident angles. This mode uses two ranges of incident angles, not including Brewster's angle, and is shown in FIG. 6. The first range of incident angles is from zero degrees to 40 degrees. The second range of incident angles is from 55 degrees to 75 degrees. In this embodiment, Brewster's angle is at 56.3 degrees. In this example, the illumination uses all azumuthal angles to produce two uniform rings of p-polarized light. In this example, the energy reflected from the film is constant for thicknesses variations from approximately 470 nm to 500 nm.

Figure 7:
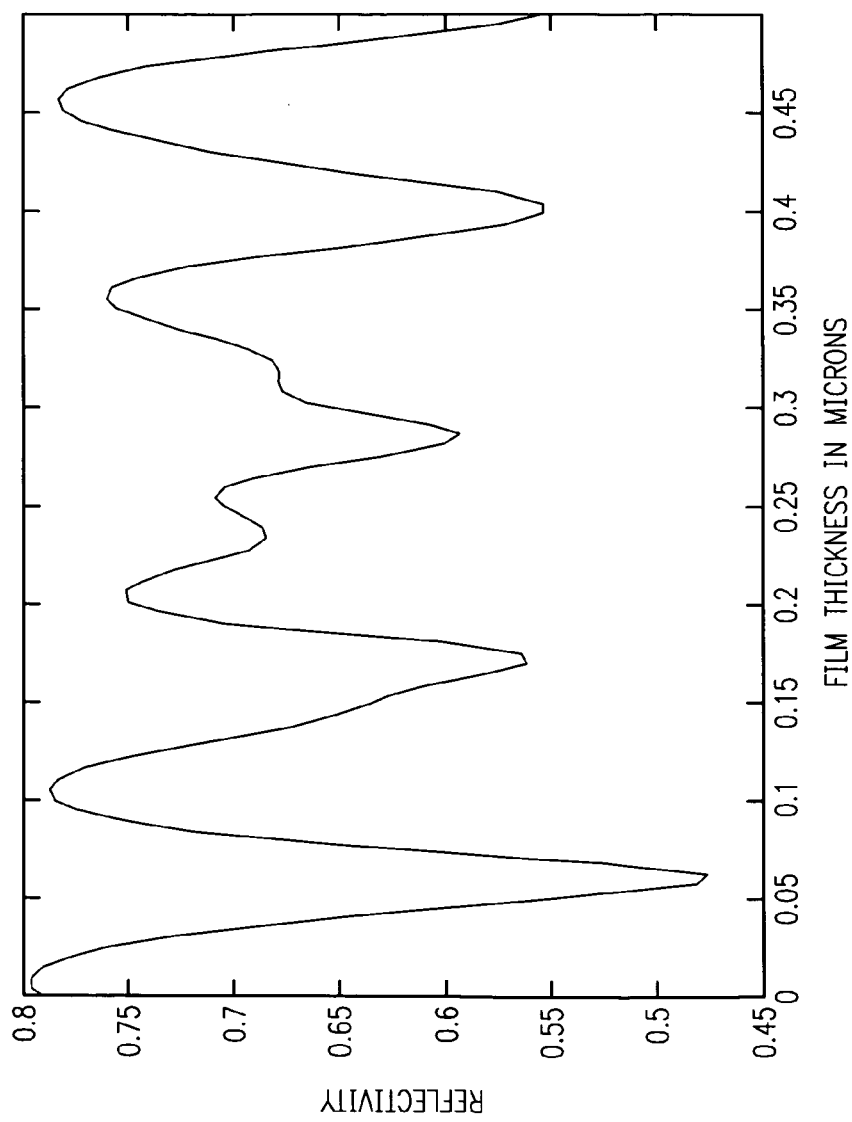
FIG. 7 is a graph of reflectivities for one inner p-polarization ring and one outer s-polarization ring for silicon dioxide film on silicon substrate.

A fourth embodiment is an illumination mode that uses two ranges of incident angles. In this mode, variations in the energy reflected from one range of incident angles compensate for the variations in the energy reflected from another range of incident angles. This mode uses two incident angle ranges where each range uses a different polarization. For example, one incident angle range can use p-polarization and the other can use s-polarization. FIG. 7 shows one example where a first range uses a p-polarization ring and includes incident angles from zero to 33 degrees and a second range uses an s-polarization ring includes incident angles from 56 through 72 degrees. The energy reflected from the sample is constant for film thicknesses of approximately 310 nm through 325 nm.

Figure 8:
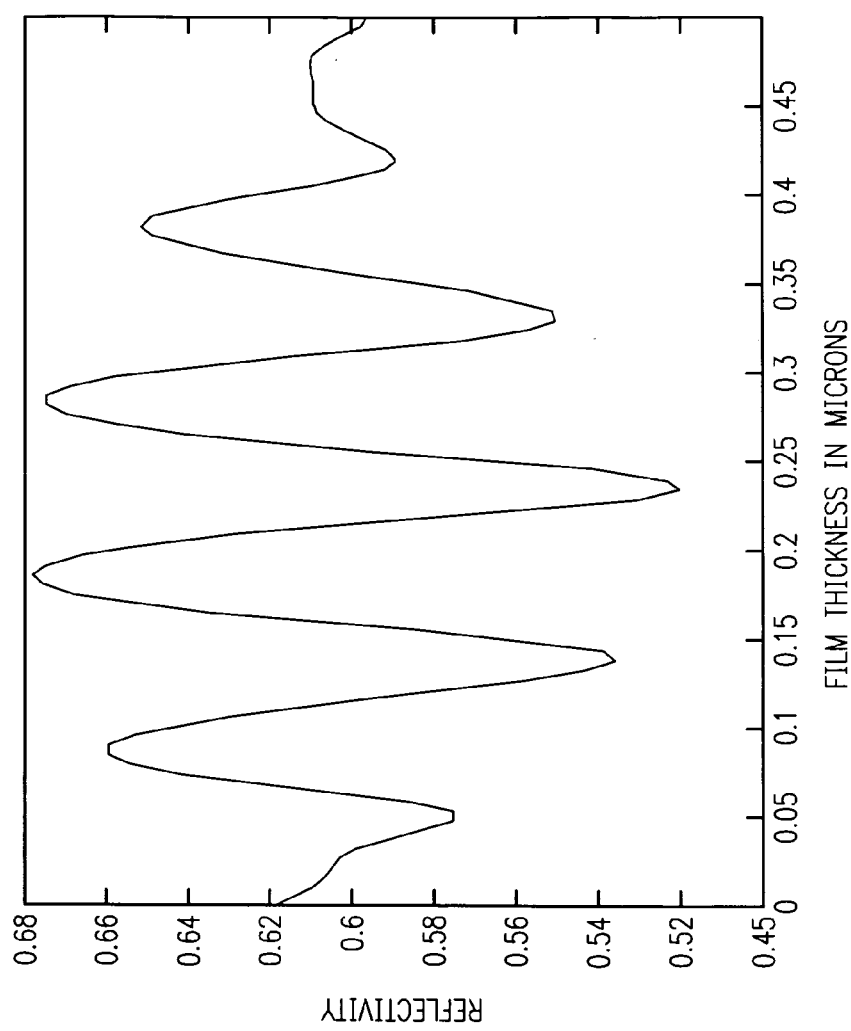
FIG. 8 is a graph of reflectivities for one inner s-polarization ring and one outer p-polarization ring for silicon dioxide film on silicon substrate.

A fifth embodiment is an illumination mode that uses two ranges of incident angles for illumination. In this mode, variations in the energy reflected from one range of incident angles can compensate for variations in the energy reflected from another range of incident angles. This mode is shown in FIG. 8 where the first range of incident angles is an s-polarized ring including incident angles from zero to 33 degrees and the second range of angles is a p-polarized ring including incident angles from 56 through 71.5 degrees. The energy reflected from the sample is constant for film thicknesses of approximately 450 nm through 480 nm.

Figure 9:
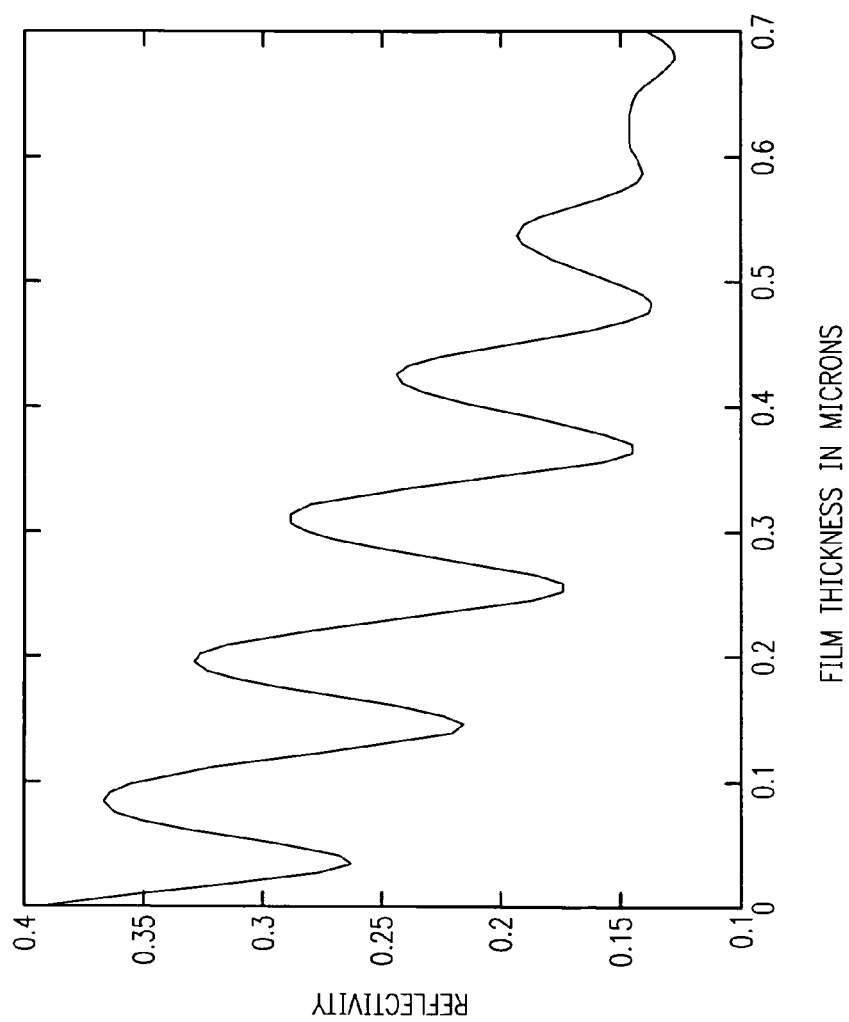
FIG. 9 is a comparison of linear polarization and 2-p-polarization rings.

A sixth embodiment is an illumination mode again using two ranges of incident angles. In this mode variations in the energy reflected from one range of incident angles compensates for the variations in the energy reflected from the other range of incident angles. This mode compensates for variations in the reflected energy from a low-k dielectric film on copper as is shown in FIG. 9, where the illumination uses two p-polarized rings. The first ring has angles of incidence from zero to 30 degrees. The second ring has angles of incidence from 44 to 72 degrees. The energy reflected by the low-k dielectric film on copper is constant for thicknesses from 610 nm to 640 nm.

Figure 10:
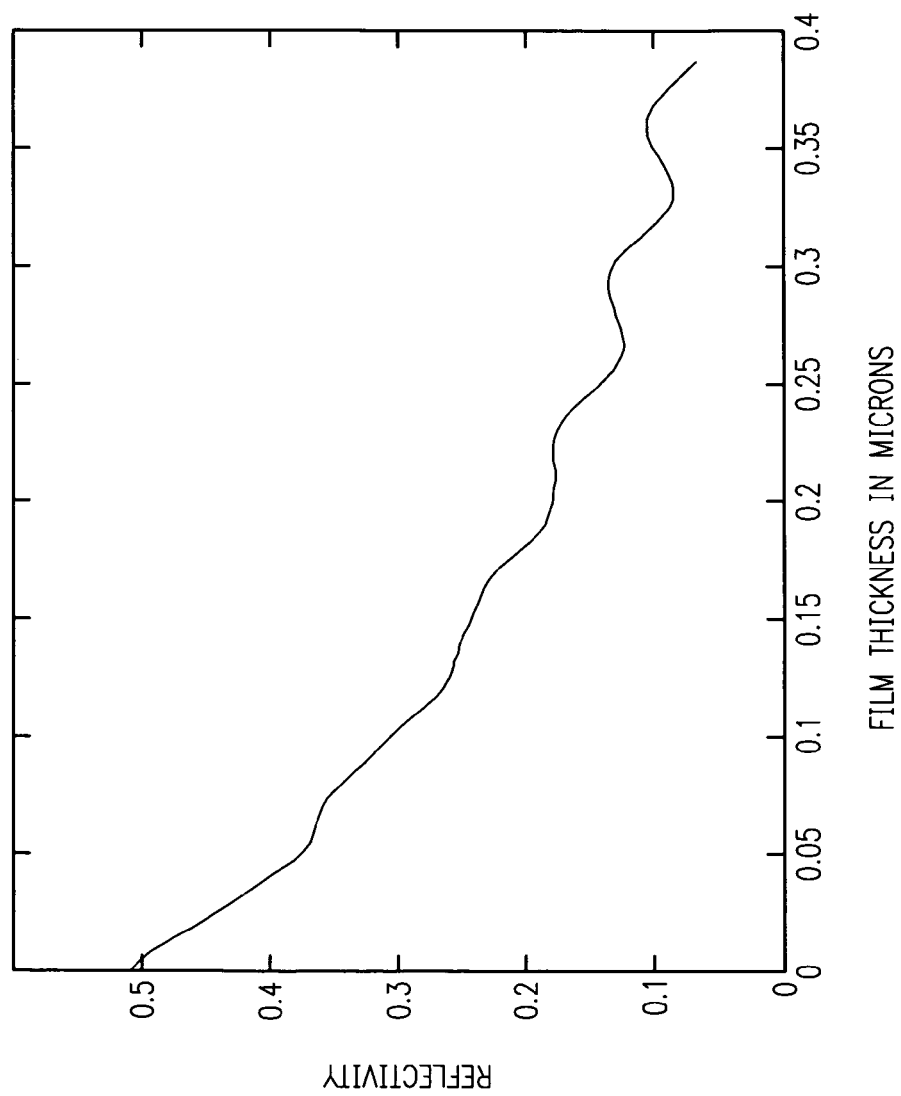
FIG. 10 is a comparison of linear polarization and one-p-polarization ring with photoresist at 193 nm.

A seventh embodiment includes another use of two ranges of incident angles. Variations in the energy reflected from one range of incident angles compensate for variations in the energy reflected from another range of incident angles. This illumination mode compensates for variations in the energy reflected from, for example, a 193 nm photoresist film on polysilicon as is shown in FIG. 10. FIG. 10 shows the variation using the p-polarization ring illumination mode with incident angles from 51.5 to 70 degrees. Here the energy reflected by photoresist thicknesses from 200 to 225 nm is relatively constant. Energy reflected from the sample can be relatively constant for other film thicknesses based on the illumination angles employed.

Figure 11:
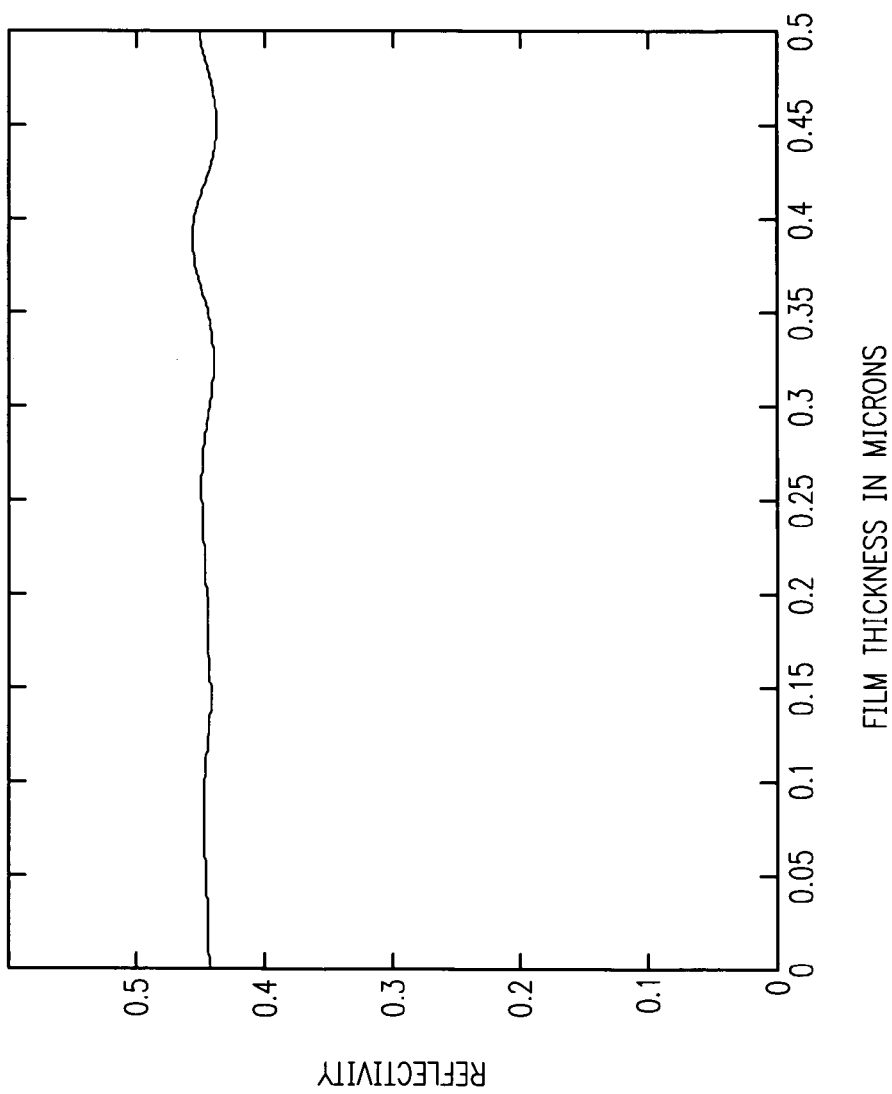
FIG. 11 shows use of 2 p-polarized rings with different wavelengths.

An eighth embodiment of the present design again uses two different wavelengths in each of the incident angle ranges. Variations in the energy reflected from one range of incident angles compensates for the variations in the energy reflected from another range of incident angles. The result of using this type of illumination is shown in FIG. 11. From FIG. 11, both rings illuminate the sample with incident angles from 50 to 62.5 degrees. One ring uses a wavelength of 266 nm and the other uses a wavelength of 355 nm. This illumination mode has similar performance to the single wavelength ring presented in FIG. 5. For certain thickness ranges, this design has less variation in the energy reflected from the sample. Using different wavelengths in this design can also aid in classifying defects.

Figure 12:
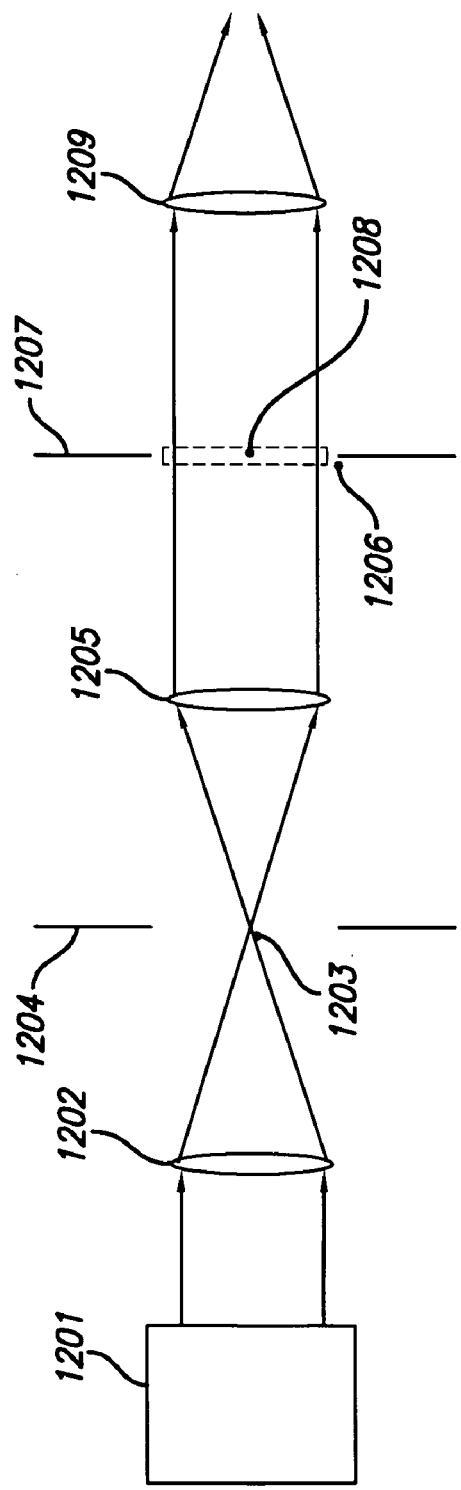
FIG. 12 is an illumination system that employs the present design.

FIG. 12 shows a schematic for a typical illumination system that can control the polarization and illumination angles delivered to the sample in the manner discussed with respect to the foregoing embodiments. Illumination light from source 1201 is collected by lens 1202 and forms an internal field 1203. An aperture 1204 can be placed at the internal field location 1203 to control the size of the illumination area on the sample. Field light energy can then be collected by lens 1205 which forms a pupil at location 1206. Apertures 1207 can be placed at this location to control illumination angles. Alternately, diffractive optics or axicons can be used to control the angles of the illumination light more efficiently than an aperture. Control using diffractive optics or axicons can require additional optical components. Polarization modifying optical elements 1208 can also be placed in proximity to the pupil location to modify the incident polarization and produce the desired polarization on the sample. Controlled and modified light from the pupil plane 1206 is then collected by lens 1209 and relayed to the imaging objective. Typically the pupil plane 1206 will be imaged to the pupil plane of the imaging objective.

Two polarizations that can reduce the effects of thin film interference are p-polarization and s-polarization. These polarizations are symmetric about the optical axis. The electric field vector for s-polarization is perpendicular to that of p-polarization. Producing these types of polarization can be difficult. Typical laser sources are either linearly polarized or have random polarization. However, laser cavities have been demonstrated that can produce p-polarization in a ring intensity profile. This type of laser source can efficiently produce the ring p-polarized illumination without the aid of additional components. Birefringent elements can also change the polarization of a laser. For example, linear polarization can be rotated using a half waveplate. A segmented waveplate can be used in combination with linear polarization to produce a polarization that is very close to p-polarization or s-polarization.

Figure 13:
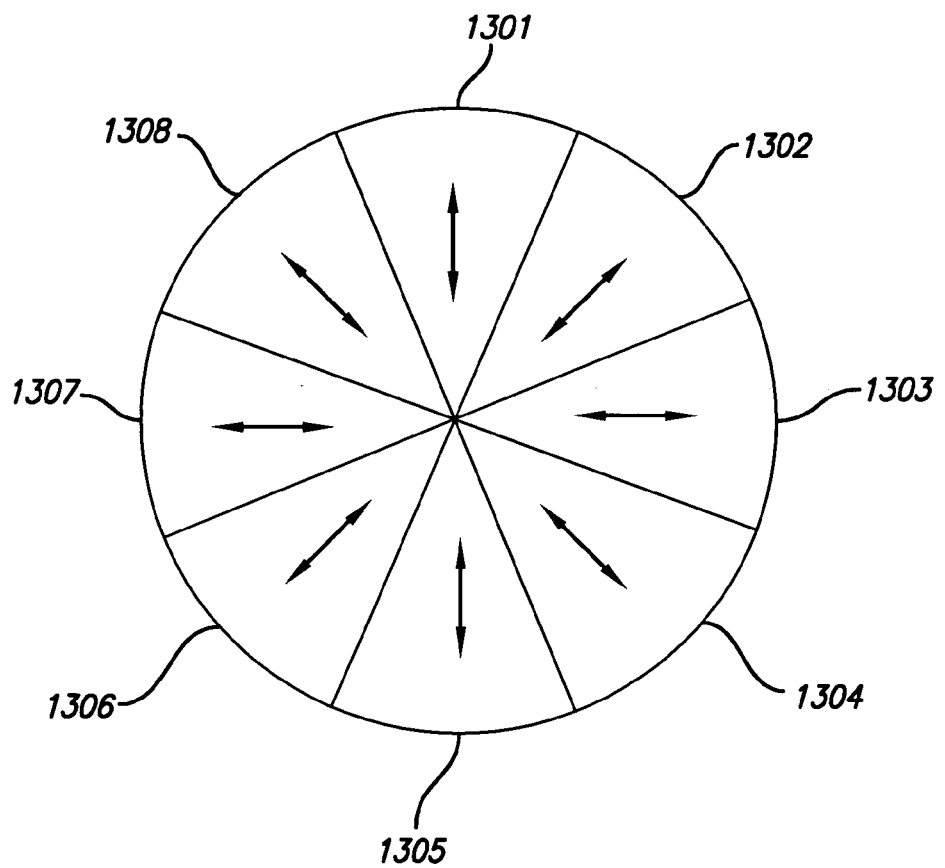
FIG. 13 shows a segmented waveplate used to produce p or s polarization from linear polarization.
Figure 14:
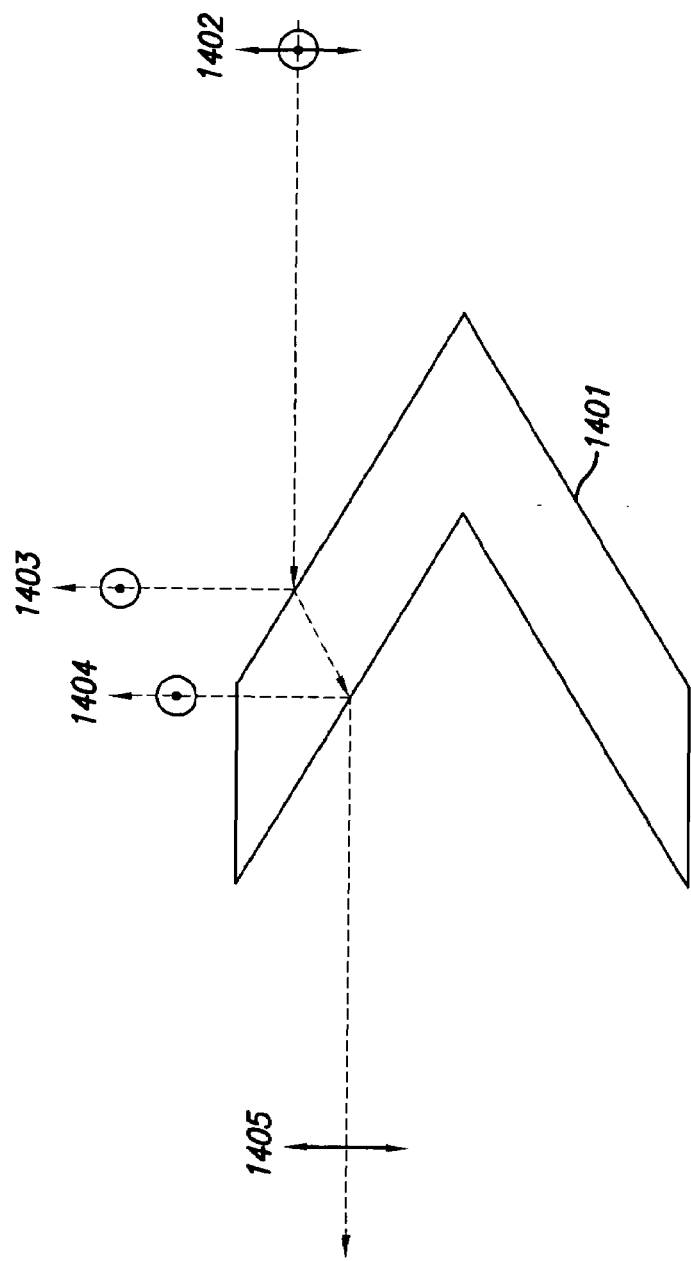
FIG. 14 is a Brewster's angle axicon with polarizing coatings to produce p-polarization.

An example of this type of segmented waveplate having eight segments is shown in FIG. 13. In this arrangement, half waveplates are fashioned into segments. Each segment may have the correct fast axis orientation and provide the desired polarization rotation. For example, segments 1301 and 1305 do not need waveplate segments present if they are aligned with the incident polarization. Alternatively, these segments may be half wave plates with the fast axis at zero degrees to the incident polarization. Segments 1302 and 1306 may be waveplates with the fast axis rotated at 22.5 degrees. Segments 1303 and 1307 are waveplates with the fast axis rotated at 45 degrees, and segments 1304 and 1308 are waveplates with the fast axis rotated at 67.5 degrees. This segmented waveplate may be used to change from p-polarization to s-polarization by rotating the angle of the incident linear polarization.

P-polarization may be obtained in various ways, including but not limited to using a mosaic of waveplates, directly from a laser, using an axicon, using form birefringence, using a diffractive element or a computer generated hologram, and using a plastic sheet polarizer. P-polarization may be produced by a laser using an axicon at Brewster's angle, with reflection coatings to enhance the reflectivity of the s-polarized light. In such a construction, randomly or circularly polarized light 1402 is incident on axicon 1401. Light from the first surface reflects the s-polarization to direction 1403 and likewise the second surface reflects the residual s-polarization to direction 1404. The remaining p-polarized light is transmitted to element 1405. Further, with respect to illumination, such illumination employed with the present design may include quatrupole illumination.

Thin film may be fashioned using various materials, including but not limited to polysilicon, silicon, oxide, low-k dielectric, high k dielectric, photoresist, spin on glass, and nitride. A layer under the thin film may be composed predominantly of a metal, such as aluminum or copper. Other metals may be used. Alternately, the layer below may be a semiconductor or semiconductor material, such as silicon.

While the invention has been described above by reference to certain embodiments, it will be understood that changes and modifications may be made without departing from the scope of the invention, which is to be defined only by the appended claims and their equivalents. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

What is claimed is:

1. A method to reduce variations in total reflected energy due to thin film interference when inspecting a sample, comprising:
   producing p-polarized light based on at least one from a group comprising linear, circular, and random polarized light; and
   illuminating the sample at an incident angle similar to Brewster's angle for a top most film, wherein said illuminating uses p-polarized light from said producing;
   wherein the incident angle, polarization of the p-polarized light, and illumination wavelength of the p-polarized light are configured to be selectively altered based on thin film interference encountered on the sample.

2. The method of claim 1 where the illuminating is quatrupole illumination.

3. The method of claim 1 wherein illumination from said illuminating comprises a ring with a range of incident angles both greater than and less than Brewster's angle.

4. The method of claim 3 where the variation in total reflected energy at incident angles less than Brewster's angle is used to balance the variation in the total reflected energy at angles greater than Brewster's angle.

5. The method of claim 1 where p-polarization is obtained by using a mosaic of waveplates.

6. The method of claim 1 where p-polarization is obtained directly from a laser.

7. The method of claim 1 where p-polarization is obtained using an axicon.

8. The method of claim 1 where p-polarization is obtained using form birefringence.

9. The method of claim 1 where p-polarization is obtained using a diffractive element.

10. The method of claim 1 where p-polarization is obtained using a plastic sheet polarizer.

11. A method to reduce variations in total reflected energy due to thin film interference when inspecting a sample, comprising:
    illuminating the sample using ring illumination provided using two light energies of different polarizations produced using at least one segmented waveplate, providing variation in total reflected energy at a first incident angle range to balance variation in total reflected energy at a second incident angle range;
    and further comprising transmitting light energy having a first polarization at the first incident angle range and light energy having a second polarization at the second incident angle range.

12. The method of claim 11 where each incident angle range uses azimuthal ring illumination.

13. The method of claim 12 where each incident angle range includes a range of incident angles.

14. The method of claim 13 where one range of incident angles is p-polarized and another range is s-polarized.

15. The method of claim 13 where both ranges of incident angles are s-polarized.

16. The method of claim 13 where both ranges of incident angles are p-polarized.

17. The method of claim 14 where s-polarized light comes from a first laser pulse and p-polarized light comes from a second laser pulse.

18. The method of claim 11, wherein said illuminating employs light energy comprising at least one from a group comprising linearly, circularly, or randomly polarized light transformed into one from a group comprising p polarization and s polarization.

19. A method for inspecting a sample, comprising:
    producing p-polarized light based on at least one from a group comprising linear, circular, and random polarized light;
    illuminating the sample at an incident angle, wherein said illuminating uses p-polarized light from said producing, and
    additionally illuminating the sample at a second incident angle, wherein further illumination at said second incident angle differs in wavelength from illumination at the incident angle;
    wherein the first incident angle, second incident angle, polarization of the p-polarized light, and illumination wavelength of the p-polarized light are configured to be selectively altered based on thin film interference encountered on the sample.

20. The method of claim 19, wherein said producing and said illuminating reduces variations in total reflected energy due to thin film interference during inspection.

21. The method of claim 19, wherein the incident angle is similar to Brewster's angle.

22. The method of claim 21, wherein illumination from said illuminating comprises a ring with a range of incident angles both greater than and less than Brewster's angle.

23. The method of claim 20, where variation in total reflected energy at incident angles less than Brewster's angle is used to balance variation in the total reflected energy at angles greater than Brewster's angle.

* * * * *